(12) United States Patent
Bewick-Sonntag et al.

(10) Patent No.: US 6,232,521 B1
(45) Date of Patent: May 15, 2001

(54) ABSORBENT ARTICLES HAVING FLUID CONTACT ANGLE GRADIENTS

(75) Inventors: Christopher Philip Bewick-Sonntag, Pescara (IT); Michael Divo, Friedrichsdorf (DE); Paolo Veglio, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/091,861

(22) PCT Filed: Dec. 19, 1996

(86) PCT No.: PCT/US96/20685

§ 371 Date: Jun. 25, 1998

§ 102(e) Date: Jun. 25, 1998

(87) PCT Pub. No.: WO97/24096

PCT Pub. Date: Jul. 10, 1997

(30) Foreign Application Priority Data

Dec. 28, 1995 (EP) .................................................. 95120652

(51) Int. Cl.[7] .................................................. A61F 13/46
(52) U.S. Cl. .............. 604/378; 604/385.01; 604/385.23; 604/385.101; 604/358
(58) Field of Search ................................. 604/378, 385.1, 604/385.2, 385.101, 385.01, 385.23

(56) References Cited

U.S. PATENT DOCUMENTS

| | | | |
|---|---|---|---|
| 3,881,489 | * | 5/1975 | Hartwell ................................ 128/287 |
| 4,591,523 | * | 5/1986 | Thompson ............................ 428/131 |
| 4,704,107 | * | 11/1987 | Coates .................................... 604/357 |
| 4,842,596 | * | 6/1989 | Kielpikowski et al. ........... 604/385.2 |
| 5,006,187 | * | 4/1991 | Cook et al. ...................... 156/244.11 |
| 5,334,177 | * | 8/1994 | Cohen ................................... 604/378 |
| 5,525,407 | * | 6/1996 | Yang ..................................... 604/378 |
| 5,603,707 | * | 2/1997 | Trombetta et al. .................... 604/378 |
| 5,643,239 | * | 7/1997 | Bodford et al. ...................... 604/370 |
| 5,762,643 | * | 6/1998 | Ray et al. ............................. 604/383 |
| 5,830,555 | * | 11/1998 | Srinivasan et al. .................. 428/137 |
| 5,928,209 | * | 7/1999 | Bodford et al. ...................... 604/370 |
| 5,990,376 | * | 11/1999 | Inoue et al. ............................ 604/378 |
| B1 6,177,607 | * | 1/2001 | Blaney et al. ........................ 604/378 |

\* cited by examiner

Primary Examiner—Aaron J. Lewis
Assistant Examiner—Michael Bogart
(74) Attorney, Agent, or Firm—Theodore P. Cummings; Matthew P. Fitzpatrick; Kevin C. Johnson

(57) ABSTRACT

The present invention relates to a disposable absorbent article (1) comprising a liquid pervious top sheet (2), an absorbent core (4), and a back sheet (3). Said back sheet comprises a fluid permeable polymeric film having uni-directional fluid transfer towards the core, and said core comprising a fluid storage layer, wherein said absorbent article exhibits a fluid contact angle gradient across said storage layer and said back sheet.

23 Claims, 3 Drawing Sheets

ABSORBENT ARTICLES HAVING FLUID CONTACT ANGLE GRADIENTS

FIELD OF THE INVENTION

The present invention relates to absorbent article in particular sanitary napkins having a breathable backsheet which exhibit reduced wet through onto the users garments.

BACKGROUND OF THE INVENTION

The primary consumer needs which underlie development in the absorbent article field, in particular catamenials is a high protection and comfort level.

One highly desirable means of improving the comfort of absorbent articles is the use of so called 'breathable backsheets'. Breathable backsheets may comprise an apertured formed film having directional fluid transfer as disclosed in for example U.S. Pat. No. 4,591,523. Such apertured breathable backsheets are typically vapour and air permeable allowing gaseous exchange with the environment. This thereby allows for the evaporation of a portion of the fluid stored in the core and increases the circulation of air within the absorbent article. This is particularly beneficial as it reduces the sticky feeling experienced by many wearers during use, particularly over extended periods of time.

However, the main drawback associated with the use of breathable backsheets in absorbent article is the increased probability of leakage, commonly referred to as wet through onto the users garment. Although such breathable backsheets in principle only allow the transfer of materials in the gaseous state and only one directional fluid transfer, physical mechanisms such as extrusion, diffusion and capillary action may still occur and result in the transfer of the fluids in the opposing direction through the backsheet and onto the users garments. In particular, these mechanisms become more dominant if the product is utilised during physical exertion, for heavy discharge loads or over extended periods of time. In effect, while breathable backsheets provide excellent comfort improvements they result in an unacceptable level of failure with regard to protection, especially under stressed conditions.

The problem of wet through onto users garments due to the incorporation of such breathable backsheets in absorbent articles has been recognized in the art. Attempts to solve the problem have mainly resided in the use of multiple layer backsheets such as those illustrated in U.S. Pat. No. 4,341,216. Similarly unpublished European patent application no. 94203230 discloses breathable absorbent articles comprising a breathable backsheet consisting of at least two breathable layers which are unattached to one another over the core area. Also unpublished European patent application no. 94203228 discloses a breathable backsheet for disposable absorbent articles comprising an outer layer of a gas permeable, hydrophobic, polymeric fibrous fabric and an inner layer comprising an apertured formed film having directional fluid transport.

Alternatively, another proposed solution to the problem has been to increase the thickness of the absorbent articles, which is usually achieved by increasing the core thickness in order to ensure the desired protection level.

However, none of the above solutions have proved fully satisfactory. This is particularly the case for thin products, as thickness is also considered as a key variable affecting product comfort. Thus, there exists a dichotomy in the methods available to provide increased comfort absorbent products, such that thin breathable products cannot provide the desired level of protection.

As a result, there exists a need to provide an absorbent article which offers improved comfort by the employment of a breathable backsheet and having a reduced thickness which maintains the required level of protection.

It has now been found that breathable backsheets may be utilised in thin sanitary napkins, thereby providing both a high level of protection and comfort by creating a hydrophobicity gradient between the backsheet and the core, achieved by the utilisation of a low surface energy material such as silicone and chlorofluorocarbons or a low surface energy treatment. In this manner it is believed that the physical mechanisms such as diffusion and capillary action are hindered and wet through is considerably reduced if not completely eliminated A further advantage of the present invention is that, since it allows to provide breathable backsheets coated with the hydrophobic material, it is no longer necessary that this layer be entirely synthetic and it may be at least partially naturally derived. This provides an important consumer noticeable benefit as the product imparts a more natural feel to the touch.

The use of surface energy gradients as such is discussed in unpublished U.S. application Ser. No. 08/442,935. It discloses fluid transport webs, e.g. topsheets, which exhibit surface energy gradients. The web facilitates fluid transport in one direction and resists transport in the opposite direction. The web comprises first and second surfaces, which are separated from one another by an intermediate portion. The first surface of the web has a lower surface energy than the surface energy of the intermediate, thereby creating a surface energy gradient. Suitable low surface energy materials include silicone, fluoropolymers and paraffins. The web is particularly suited as a topsheet for absorbent articles in order to transport fluid away from the wearer-contacting surface into the absorbent structure.

SUMMARY OF THE INVENTION

The first aspect of the present invention relates to a disposable absorbent article comprising, a liquid pervious topsheet, an absorbent core and a backsheet. The core is intermediate the topsheet and the backsheet. The backsheet comprises a liquid permeable polymeric film having unidirectional fluid transfer towards the core, and the core comprises a fluid storage layer and the backsheet comprises an outer layer. The core and the backsheet each comprise at least one layer, wherein each layer has a wearer facing surface and a garment facing surface and each surface of these layers has a fluid contact angle. The absorbent article has a lower portion extending from and including the garment facing surface of the fluid storage layer to and including the garment facing surface of the outer layer. The present invention is characterized in that the wearer facing surface of at least one of the layers in the lower portion has a fluid contact angle greater than the fluid contact angle of the adjacent garment facing surface of an adjacent layer.

A second aspect of the present invention relates to the situation wherein the garment facing surface of at least one of the layers in the lower portion has a fluid contact angle greater than the fluid contact angle of the wearer facing surface of the same layer.

A further aspect of the present invention relates to a process for the production of an absorbent article described above comprising the step of applying a low surface energy material to the surface of at least one of the layers in the lower portion.

Another aspect of the present invention relates to a process for the production of an absorbent article described above comprising the step of incorporating a low surface energy material within one of the layers in the lower portion.

DETAILED DESCRIPTION OF THE INVENTION

Figure 1:
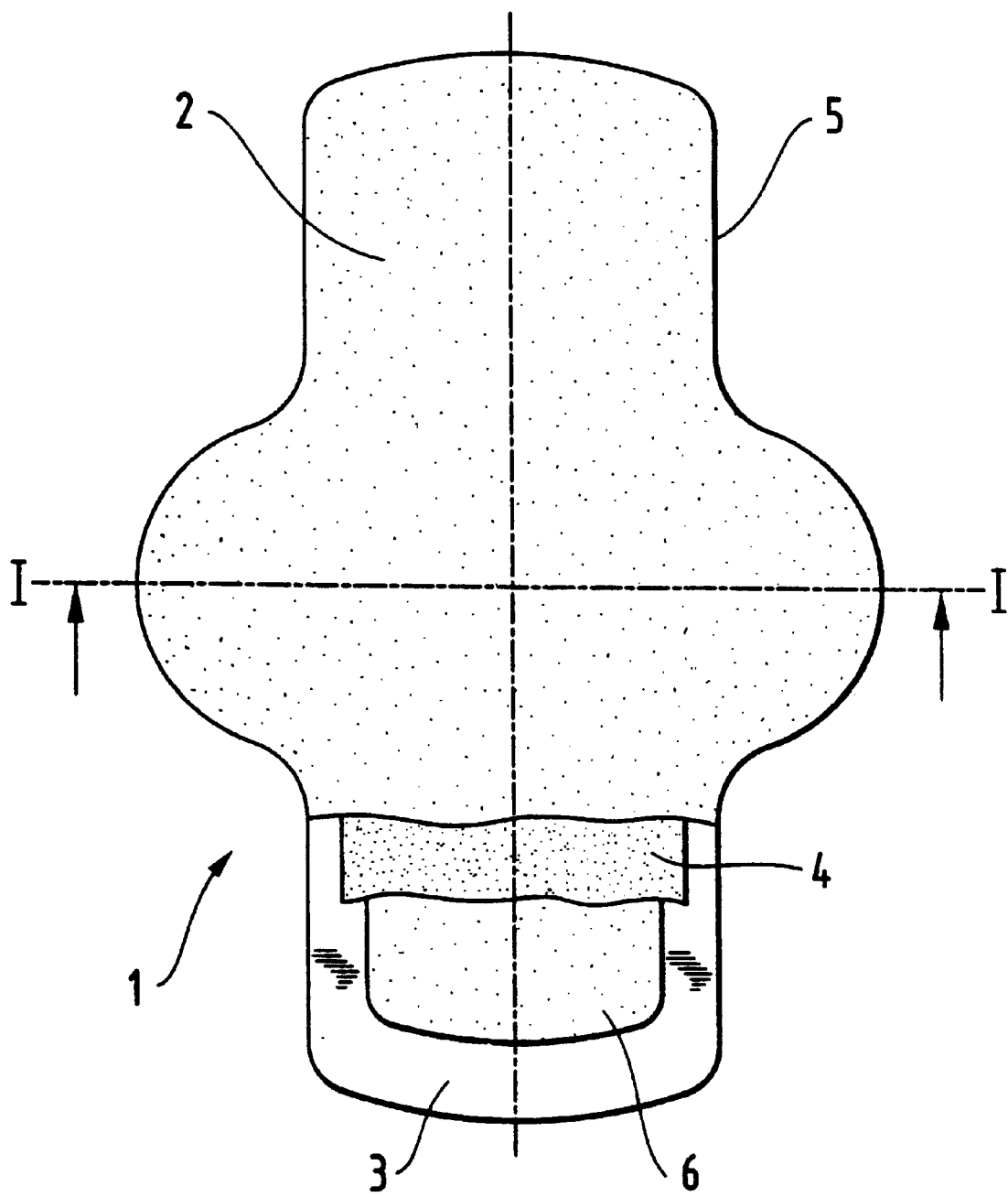
FIG. 1: Top plan view of a first embodiment of an absorbent article of the present invention with portions cut away to show its construction.

The present invention relates to absorbent disposable articles such as sanitary napkins (1), baby diapers, incontinence products and panty liners. Typically such products comprise a liquid pervious topsheet (2), a backsheet (3) and an absorbent core (4) intermediate said topsheet (2) and said backsheet (3). The topsheet (2), backsheet (3) and core (4) each have a wearer facing surface and a garment facing surface. The garment facing surface of the topsheet and the wearer facing surface of the backsheet are joined to one another at the periphery (5) of said absorbent article. In a preferred embodiment of the present invention the absorbent article has wings, side wrapping elements or sideflaps.

Absorbent Core

According to the present invention, the absorbent core comprises a first portion and a second portion, said first portion comprising the following components: (a) an optional primary fluid distribution layer preferably together with a secondary optional fluid distribution layer; (b) a fluid storage layer; and said second portion comprising (c) an optional fibrous ("dusting") layer underlying the storage layer; and (d) other optional components.

According to the present invention the absorbent core may have any thickness depending on the end use envisioned. In a preferred embodiment of the present invention wherein the absorbent article is a sanitary napkin or a panty liner, the core may have a thickness of from 15 mm to 1 mm, preferably from 10 mm to 1 mm, most preferably from 7 mm to 1 mm.

a Primary/Secondary Fluid Distribution Layer

One optional component of the first portion of the absorbent core according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilised. The fluid distribution layers can be comprised of any material typical for such distribution layers.

b Fluid Storage Layer

Positioned in fluid communication with, and typically underlying the primary or secondary distribution layers, is a fluid storage layer (6). The fluid storage layer can comprise any usual absorbent material or combinations thereof. It preferably comprises absorbent gelling materials usually referred to as "hydrogel", "superabsorbent", hydrocolloid" materials in combination with suitable carriers.

The absorbent gelling materials are capable of absorbing large quantities of aqueous body fluids, and are further capable of retaining such absorbed fluids under moderate pressures. The absorbent gelling materials can be dispersed homogeneously or non-homogeneously in a suitable carrier. The suitable carriers, provided they are absorbent as such, can also be used alone.

Suitable absorbent gelling materials for use herein will most often comprise a substantially water-insoluble, slightly cross-linked, partially neutralised, polymeric gelling material. This material forms a hydrogel upon contact with water. Such polymer materials can be prepared from polymerizable, unsaturated, acid-containing monomers which are well known in the art.

Suitable carriers include materials which are conventionally utilised in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins and panty liners.

An embodiment of the absorbent structure made according to the present invention comprises a double layer tissue laminate formed by folding the tissue onto itself. These layers can be joined to each other for example by adhesive or by mechanical interlocking or by hydrogen bridge bonds. Absorbent gelling material or other optional material can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the absorbent gelling material is dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing absorbent gelling materials partially or fully.

c Optional Fibrous ("Dusting") Layer

An optional component for inclusion in the absorbent core according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting"

layer provides some additional fluid-handling capabilities such as rapid wicking of fluid along the length of the pad.

d Other Optional Components of the absorbent structure

The absorbent core according to the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

Another component which can be included in the absorbent core according to the invention and preferably is provided close to or as part off the primary or secondary fluid distribution layer are odor control agents. Active carbon coated with or in addition to other odor control agents, in particular suitable zeolite or clay materials, are optionally incorporated in the absorbent structure. These components can be incorporated in any desired form but often are included as discrete particles.

The topsheet

The topsheet (21) may comprise a single layer or a multiplicity of layers. In a preferred embodiment the topsheet comprises a first layer (22) which provides the wearer facing surface of the topsheet and a second layer (23) between the first layer and the absorbent structure/core.

The topsheet (21) as a whole and hence each layer individually needs to be compliant, soft feeling, and non-irritating to the wearer's skin. It also can have elastic characteristics allowing it to be stretched in one or two directions. According to the present invention the topsheet may be formed from any of the materials available for this purpose and known in the art, such as non woven fabrics, films or combinations of both. In a preferred embodiment of the present invention at least one of the layers (preferably the upper layer) of the topsheet comprises a liquid permeable apertured polymeric film (22).

Preferably, the upper layer is provided by a film material having apertures which are provided to facilitate liquid transport from the wearer facing surface towards the absorbent structure, as detailed for example in U.S. Pat. Nos. 3,929,135, 4,151,240 4,319,868, 4,324,426, 4,343,314 and 4,591,523.

The topsheet typically extends across the whole of the absorbent structure and can extend into and form part of or all of the preferred sideflaps, side wrapping elements or wings.

Backsheet

The absorbent articles according to the present invention comprise a uni directional fluid transfer breathable backsheet (24). The primary role of the backsheet is to prevent the extrudes absorbed and contained in the absorbent structure from wetting articles that contact the absorbent product such as underpants, pants, pajamas and undergarments. In addition however, the backsheet of the absorbent article of the present invention also permits the transfer of both vapour and air through it and thus allows the circulation of air into and out of the backsheet.

The term "uni-directional" as utilized herein refers to materials which have at least a substantially, if not complete, one directional fluid transport in the direction of the core. Fluid directionality may be identified using the test method 3 detailed herein under test methods.

According to the present invention the backsheet preferably comprises at least two layers; a first layer comprising a gas permeable apertured polymeric film (25) and a second layer comprising a gas permeable fibrous fabric layer (26). Said first and second layers preferably have a similar relative void volume. Said first layer is typically located adjacent to said core (27) and subsequent layers of the backsheet are typically located further away from said core. The backsheet may comprise additional layers. In all cases the outermost layer furthest away from the core is the outer layer. All of the layers of the backsheet can be substantially in intimate and direct contact with one another.

The apertured first layer of the backsheet (25) comprises a layer having discrete apertures (28) which extend beyond the horizontal plane of the garment facing surface of the layer towards the core thereby forming protuberances (29). Each protuberance has an orifice located at its terminating end. Preferably said protuberances have a funnel or conical shape, similar to those described in U.S. Pat. No. 3,929,135. The apertures located within the plane of the layer and the orifices located at the terminating end of protruberance themselves maybe circular or non-circular. In any case the cross sectional dimension or area of the orifice at the termination of the protuberance is smaller than the cross sectional dimension or area of the aperture located within the plane of the layer. The first layer of the backsheet typically has an open area of more than 5%, preferably from 10% to 35% of the total film layer area. The open area of the layer can be determined using the test method 4 detailed herein under test methods.

According to the present invention said first layer of the backsheet (25) may be made of any material known in the art, but is preferably manufactured from commonly available polymeric materials.

The second layer of said backsheet comprises a gas permeable fibrous fabric layer (26) composed of polymeric fibers such as polymeric non-wovens known in the art. The fibrous fiber layer preferably has a basis weight of 10 to 100 $g/m^2$, more preferably 15 to 30 $g/m^2$. The fibers can be made of any polymeric material, in particular, fibers of polyethylene, polypropylene, polyester polyacetate or combinations thereof (inter- and intra fiber combinations) and also mixtures of synthetic fibers and non absorbent natural fibers or treated natural fibers such as cotton may be utilized. The fibers are preferably spunbonded, carded or melt blown. Preferably the second layer comprises a matrix of spun-bonded fibers covered on one side with meltblown fibers or alternatively a matrix of meltblown fibers covered on both sides with spun blown fibers. The second layer of the backsheet may in addition comprise at least 5% by weight of said layer of fibers which are liquid absorbtive such that the fibers swell and reduce inter-fiber spacing.

The backsheet typically extends across the whole of the absorbent structure and can extend into and form part of or all of the preferred sideflaps, side wrapping elements or wings.

Fluid contact angle

According to the first aspect of the present invention any layer in the lower portion has a wearer facing surface and a garment facing surface and each of said surfaces has a fluid contact angle, wherein the wearer facing surface of at least one of said layers in said lower portion has a fluid contact angle greater than the fluid contact angle of the garment facing surface of the adjacent garment facing surface of an adjacent layer.

According to the second aspect of present invention any layer in said lower portion has a wearer facing surface and a garment facing surface and each of said surfaces of said layers has a fluid contact angle wherein the garment facing surface of at least one of said layers in said lower portion has a fluid contact angle greater than the fluid contact angle of the wearer facing surface of said same layer.

In principle the contact angle gradient may be present in said lower portion between any surface (wearer facing or garment facing) of any layer therein. Thus, the fluid contact angle gradient may be present across the wearer and garment facing surface of the same layer or between the garment facing surface of at least one layer in the lower portion and an adjacent surface of an adjacent layer, i.e. between the wearer and the garment facing surface of the first layer of the backsheet, between the garment facing surface of the first layer and the wearer facing surface of the second layer of the backsheet, between the wearer and the garment facing surface of the second layer of the backsheet or between any subsequent backsheet layers. In addition, it is also foreseen that combinations of these layers each exhibiting a specific contact angle relation be utilised thereby producing a continuous gradient in contact angles in the lower portion.

However, for simplicity purposes the description of the invention hereinafter will focus on the presence of a distinct or increased contact angle gradient between the garment facing surface of the core and the wearer facing surface of the first layer of the backsheet.

Figure 3:
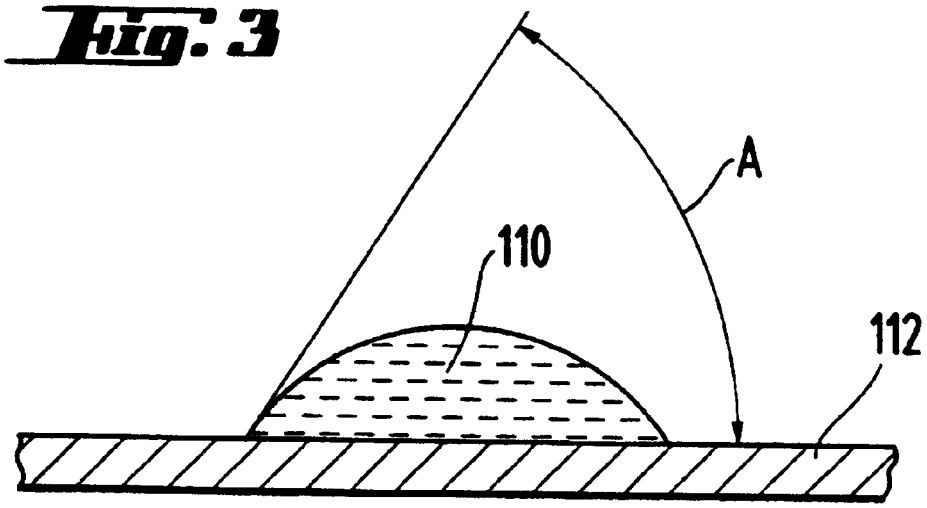
FIG. 3: An enlarged cross sectional view of a droplet of liquid on a surface, where angle A illustrates the contact angle of the liquid with the surface.

Typically, a drop of liquid 110 placed on a solid surface 112 makes a contact angle, A, with the solid surface, as seen in FIG. 3. As the wettability of the solid surface by the liquid increases, the contact angle, A, decreases. As the wettability of the solid surface by the liquid decreases, the contact angle, A, increases. The liquid-solid contact angle may be determined from techniques known in the art, such as those described in greater detail in *Physical Chemistry of Surfaces*, Second Edition, by Arthur W. Adamson (1967), F. E. Bartell and H. H. Zuidema, *J. Am. Chem. Soc.*, 58, 1449 (1936), and J. J. Bikerman, *Ind. Eng. Chem., Anal. Ed.*, 13, 443 (1941), each of which are hereby incorporated herein by reference. More recent publications in this area include Cheng, et al., *Colloids and Surfaces* 43:151–167 (1990), and Rotenberg, et al., *Journal of Colloid and Interface Science* 93(1):169–183 (1983), which are also hereby incorporated herein by reference.

As used herein, the term "hydrophilic" is used to refer to surfaces that are wettable by aqueous fluids (e.g., aqueous body fluids) deposited thereon. Hydrophilicity and wettability are typically defined in terms of contact angle and the surface tension of the fluids and solid surfaces involved. This is discussed in detail in the American Chemical Society publication entitled *Contact Angle, Wettability and Adhesion*, edited by Robert F. Gould (Copyright 1964), which is hereby incorporated herein by reference. A surface is said to be wetted by an aqueous fluid (hydrophilic) when the fluid tends to spread spontaneously across the surface. Conversely, a surface is considered to be "hydrophobic" if the aqueous fluid does not tend to spread spontaneously across the surface.

The liquid/solid contact angle depends on surface inhomogeneities (e.g., chemical and physical properties, such as roughness), contamination, chemical/physical treatment of or composition of the solid surface, as well as the nature of the liquid and its contamination. The surface energy of the solid also influences the contact angle. As the surface energy of the solid decreases, the contact angle increases. As the surface energy of the solid increases, the contact angle decreases.

The energy required to separate a liquid from a solid surface (e.g., a film or fiber) is expressed by equation (1):

$$W = G(1 + \cos A) \tag{1}$$

where:

W is the work of adhesion measured in erg/$cm^2$, (×$10^{-3}$ $Jm^{-2}$)

G is the surface tension of the liquid measured in dyne/cm, (×$10^3$ $Nm^{-1}$) and A is the liquid-solid contact angle measured in degrees.

For a given liquid, the work of adhesion increases with the cosine of the liquid-solid contact angle (reaching a maximum where the contact angle A is zero).

Work of adhesion is one useful tool in understanding and quantifying the surface energy characteristics of a given surface for a given liquid.

Table 1 is useful to illustrate the relationship between solid-liquid contact angle and work of adhesion for a particular fluid (e.g., water), whose surface tension is 75 dynes/cm (75×$10^{-3}$ $Jm^{-2}$).

TABLE 1

| A (degrees) | cos A | 1 + cos A | W (erg/cm$^2$) (×10$^{-3}$ Jm$^{-2}$) |
|---|---|---|---|
| 0 | 1 | 2 | 150 |
| 30 | 0.87 | 1.87 | 140 |
| 60 | 0.5 | 1.50 | 113 |
| 90 | 0 | 1.00 | 75 |
| 120 | −0.5 | 0.5 | 38 |
| 150 | −0.87 | 0.13 | 10 |
| 180 | −1 | 0 | 0 |

As depicted in Table 1, as the work of adhesion of a particular surface decreases (exhibiting a lower surface energy of the particular surface), the contact angle of the fluid on the surface increases, and hence the fluid tends to "bead up" and occupy a smaller surface area of contact. The reverse is likewise true as the surface energy of a given surface decreases with a given fluid. The work of adhesion, therefore, influences interfacial fluid phenomena on the solid surface.

Figure 4:
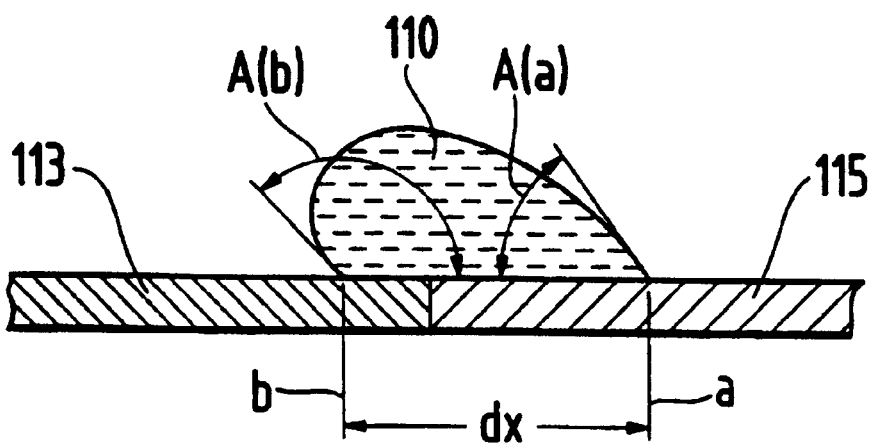
FIG. 4: An enlarged cross sectional view of a droplet of liquid on a surface having two different surface energies, thus exhibiting two different contact angles A(a) and A(b).

More importantly, in the context of the present invention, surface energy gradients as illustrated by fluid contact angles or discontinuities have been found to be useful in preventing fluid transport. FIG. 4. illustrates a droplet of fluid 110 which is located on a solid surface having two regions 113 and 115 having differing surface energies (indicated by the different cross-hatching for illustrative purposes). In the situation illustrated in FIG. 4, region 113 exhibits a comparatively lower surface energy than region 115, and hence a reduced wettability for the fluid of the droplet than region 115. Accordingly, the droplet 110 produces a contact angle A(b) at the edge of the droplet contacting region 113 which is greater than the contact angle A(a) produced at the edge of the droplet contacting region 115. It should be noted that although for graphic clarity the points "a" and "b" lie in a plane, the distance "dx" between points "a" and "b" need not be linear, instead representing the extent of droplet/surface contact regardless of the shape of the surface. Droplet 110 thus experiences a surface energy imbalance and hence an external force due to the differences in the relative surface energies (i.e., the surface energy gradient or discontinuity) between regions 113 and 115, which can be represented by the equation (2):

$$dF = G[\cos A(a) - \cos A(b)]dx \tag{2}$$

where:

dF is the net force on the fluid droplet, dx is the distance between the reference locations "a" and "b", G is as defined previously, and A(a), and A(b) are the contact angles A at locations "a" and "b", respectively.

Solving equation (1) for cos A(a) and cos A(b) and substituting into equation (2) yields equation (3):

$$dF = G[(W(a)/G-1)-(W(b)/G-1)]dx \quad (3)$$

Equation (3) can be simplified to equation (4):

$$dF = (W(a)-W(b))dx \quad (4)$$

The importance of the differential in surface energy between the two surfaces is clearly depicted in equation (4), as is the directly proportional effect that changes in the magnitude of the differential in work of adhesion would have on the magnitude of the force.

More detailed discussions of the physical nature of surface energy effects and capillarity may be found in *Textile Science and Technology*, Volume 7, *Absorbency*, edited by Portnoy K. Chatterjee (1985), and *Capillarity, Theory and Practice, Ind. Eng. Chem.* 61,10 (1969) by A. M. Schwartz, which are hereby incorporated herein by reference.

Accordingly, the force experienced by a droplet will cause movement in the direction of the surface featuring the higher surface energy in this case towards the core. For simplicity and graphic clarity, the surface energy gradient or discontinuity has been depicted in FIG. 4 as a single, sharp discontinuity or boundary between well-defined regions of constant but differing surface energy. Surface energy gradients may also exist as a continuous gradient or a step-wise gradient, with the force exerted on any particular droplet (or portions of such droplet) being determined by the surface energy at each particular area of droplet contact.

As used herein, the term "gradient" when applied to differences in surface energy or work of adhesion is intended to describe a change in surface energy or work of adhesion occurring over a measurable distance. The term "discontinuity" is intended to refer to a type of "gradient" or transition, wherein the change in surface energy occurs over an essentially zero distance. Accordingly, as used herein all "discontinuities" fall within the definition of "gradient".

Also, as used herein the terms "capillary" and "capillarity" are used to refer to passageways, apertures, pores, or spaces within a structure which are capable of fluid transport in accordance with the principles of capillarity generally represented by the Laplace equation (5):

$$p = 2G(\cos A)/R \quad (5)$$

where:

p is the capillary pressure;

R is the internal radius of the capillary (capillary radius); and

G and A are as defined above.

As noted in *Penetration of Fabrics* by Emery I. Valko, found in Chapter III of *Chem. Aftertreat. Text.* (1971), pp. 83–113, which is hereby incorporated herein by reference, for A=90°, the cosine of A is zero and there is no capillary pressure. For A>90°, the cosine of A is negative and the capillary pressure opposes the entry of fluid into the capillary. Hence, for hydrophilic aqueous liquids the capillary walls should be of a hydrophilic nature for an appreciable capillary phenomena to occur. Also, R must be sufficiently small for p to have a meaningful value, since as R increases (larger aperture/capillary structure) the capillary pressure decreases.

Perhaps at least as important as the presence of surface energy gradients is the particular orientation or location of the gradients themselves with respect to the orientation and location of the capillaries or fluid passageways themselves.

Water is used as a reference liquid throughout only as an example for discussion purposes, and is not meant to be limiting. The physical properties of water are well-established, and water is readily available and has generally uniform properties wherever obtained. The concepts regarding work of adhesion with respect to water can easily be applied to other fluids such as blood, menses and urine, by taking into account the particular surface tension characteristics of the desired fluid.

By having a surface energy gradient between the core and backsheet creating a relatively low surface energy adjacent the portion of the backsheet which will be placed adjacent to and in contact with the absorbent core, and a relatively lower surface energy portion located towards contact with the wearer's skin, the backsheet will be capable of hindering the movement of a drop of liquid from the core exhibiting the relatively higher surface energy to the backsheet exhibiting the relatively lower surface energy. The motion of the drop of liquid is induced by the contact angle differential between the lower surface energy portion and the higher surface energy portion which results in an imbalance in surface tension force acting on the solid-liquid contact plane. It is believed that this resulting surface energy gradient, which results in a negative capillary pressure is particularly suited for use with an apertured backsheet on an absorbent article, such as backsheet (2,24) on absorbent article (1).

The potential for wet through is thereby reduced by having an apertured backsheet with a surface energy gradient according to the aforementioned description. As some in-use forces tend to force the collected fluid to be squeezed out of the pad (e.g., squeezed by compression from the absorbent core towards the lower surface of the backsheet), such undesirable movement will be resisted by the surface of the backsheet which has a relatively low surface energy to repel the fluid as it attempts to make its way out of the pad through the openings in the backsheet.

Thus, the fluid is more readily retained in the absorbent core due to the driving forces of the surface energy gradients between the backsheet and core.

With regard to the surface energy gradients of the present invention, it is important to remember that the upper and lower bounds of any such gradient are relative with respect to one another, i.e., the regions of the backsheet and core whose interface defines a surface energy gradient need not be on different sides of the hydrophobic/hydrophilic spectrum. That is to say, a gradient may be established by two surfaces of diverse degrees of hydrophobicity or diverse degrees of hydrophilicity, and need not necessarily be established with regard to a hydrophobic surface and a hydrophilic surface. Notwithstanding the foregoing, it is presently preferred that the upper surface of the backsheet have a comparatively low surface energy, i.e., that it be generally hydrophobic, in order to maximize the driving force imparted to the incoming fluid from the core and minimize the overall wet through of the backsheet on the garment-contacting surface.

Accordingly, in the present invention the surface energy gradients provide a synergistic effect in combination with the one directional fluid transport nature of the backsheet to prevent fluid transport through the backsheet. Fluid on the first surface of the backsheet encounters two differing, but complementary driving forces which oppose its motion away from the core to the backsheet and towards the garment. These two forces likewise combine to oppose fluid movement toward the backsheet, thus dramatically reducing the incidence of wet through.

A number of physical parameters should be considered in designing an apertured backsheet and a core according to the absorbent article of the present invention, more particularly with regard to appropriately sizing and positioning the surface energy gradients for proper fluid handling. Such factors include the magnitude of the surface energy differential (which depends upon the materials utilized), migratability of materials, bio-compatibility of materials, porosity or capillary size, overall caliper and geometry, fluid viscosity and surface tension, and the presence or absence of other structures on either side of the interfaces.

Preferably the difference in fluid contact angle between two adjacent surfaces providing a surface energy gradient should be at least 10°, preferably at least 20° and the surface having the lower surface energy should have a fluid contact angle of at least 90°, preferably at least 100°, more preferably at least 110°, most preferably at least 120°.

Figure 2:
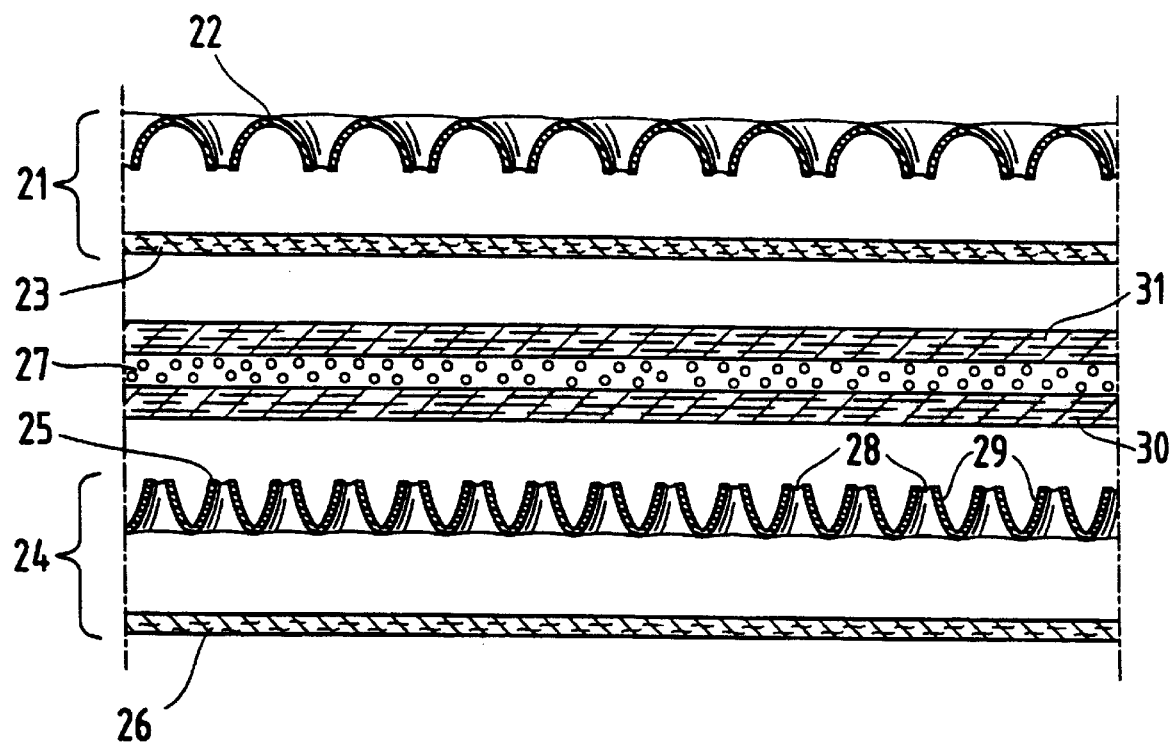
FIG. 2: Enlarged cross sectional view of a backsheet of the present invention taken along line 1—1 of FIG. 1.

According to the present invention the contact angle of a layer may be increased by rendering that surface more hydrophilic. To manufacture a backsheet depicted in FIG. 2 according to the present invention, a sheet of polyethylene is extruded onto a drum where it is vacuum formed into an apertured formed film and then, if desired, subjected to a corona discharge treatment generally in accordance with the teachings of U.S. Pat. Nos. 4,351,784 issued to Thomas et al. on Sep. 28, 1982; 4,456,570 issued to Thomas et al. on Jun. 26, 1984; and 4,535,020 issued to Thomas et al. on Aug. 13, 1985, the disclosures of each of these patents being incorporated herein by reference. A surface treatment having a relatively lower surface energy is then applied to the wearer facing surface of the apertured formed film and is preferably cured. A suitable surface treatment is a silicone release coating from Dow Corning of Midland, Mich. available as Syl-Off 7677 to which a crosslinker available as Syl-Off 7048 is added in proportions by weight of 100 parts to 10 parts, respectively. Another suitable surface treatment is a coating of a UV curable silicone comprising a blend of two silicones commercially available from General Electric Company, Silicone Products Division, of Waterford, N.Y., under the designations UV 9300 and UV 9380C-D1, in proportions by weight of 100 parts to 2.5 parts, respectively. When such a silicone blend is utilized on a formed film such as depicted in FIG. 2, coating application levels of at least 0.25 g, preferably 0.5 to 8.0 grams silicone per square meter of surface area have performed satisfactorily, although other coating levels may prove suitable for certain applications depending upon the nature of the backsheet and the characteristics of the fluid, etc.

Other suitable treatment materials include, but are not limited to, fluorinated materials such as fluoropolymers (e.g., polytetrafluoroethylene (PTFE), commercially available under the trade name TEFLON™) and chlorofluoropolymers. Other materials which may prove suitable for reduced surface energy include hydrocarbons such as petrolatum, latexes, paraffins, and the like, although silicone materials are presently preferred for use in the absorbent article context for their biocompatibility properties. As used herein, the term "biocompatible" is used to refer to materials having a low level of specific adsorption for, or in other words a low affinity for, bio-species or biological materials such as gluco-proteins, blood platelets, and the like. As such, these materials tend to resist deposition of biological matter to a greater extent than other materials under in-use conditions. This property enables them to better retain their surface energy properties as needed for subsequent fluid handling situations. In the absence of biocompatibility, the deposition of such biological material tends to increase the roughness or non-uniformity of the surface, leading to increased drag force or resistance to fluid movement. Consequently, biocompatibility corresponds to reduced drag force or resistance to fluid movement, and hence faster access of fluid to the surface energy gradient and capillary structure. Maintenance of substantially the same surface energy also maintains the original surface energy differential for subsequent or enduring fluid depositions.

Biocompatibility, however, is not synonymous with low surface energy. Some materials, such as polyurethane, exhibit biocompatibility to some degree but also exhibit a comparatively high surface energy. Presently preferred materials such as silicone and fluorinated materials advantageously exhibit both low surface energy and biocompatibility.

Another preferred method for converting a ribbon of polyethylene film into an apertured formed film is by applying a high pressure fluid jet comprised of water or the like against one surface of the film, preferably while applying a vacuum adjacent the opposite surface of the film. Such methods are described in greater detail in commonly assigned U.S. Pat Nos. 4,609,518 issued to Curro et al. on Sep. 2, 1986; U.S. Pat. No. 4,629,643 issued to Curro et al. on Dec. 16, 1986; U.S. Pat. No. 4,637,819 issued to Ouellette et al. on Jan. 20, 1987; U.S. Pat. No. 4,681,793 issued to Linman et al. on Jul. 21, 1987; U.S. Pat. No. 4,695,422 issued to Curro et al. on Sep. 22, 1987; U.S. Pat. No. 4,778,644 issued to Curro et al. on Oct. 18, 1988; U.S. Pat. No. 4,839,216 issued to Curro et al. on Jun. 13, 1989; and U.S. Pat. No. 4,846,821 issued to Lyons et al. on Jul. 11, 1989, the disclosures of each of said patents being incorporated herein by reference. The apertured formed film may, if desired, be subjected to a corona discharge treatment. A silicone release coating, may then be applied or printed onto the first surface of the apertured formed film and is preferably cured. The surface energy of the silicone-treated surface is less than the surface energy of the untreated surface of the backsheet.

Alternatively, the layer exhibiting the lower surface energy, e.g. the apertured polymeric backsheet layer may have the low surface anergy material incorporated within said layer during manufacture such that the layer is rendered hydrophobic during manufacture. This layer may then have a low surface energy material applied to its surface. Typically, said layer comprises at least 5% by total weight of said layer of a low surface energy material.

According to the present invention the absorbent article is constructed by joining the various elements such as topsheet, backsheet and absorbent core by any means well known in the art. For example the backsheet and/or topsheet may be joined to the absorbent core or to each other by a uniform continuous layer of adhesive, a patterned layer of adhesive, or any array of separate lines, spirals or spots of adhesive. Alternatively, the elements may be joined by heat bonds, pressure bonds, ultra sonic bonds, dynamic mechanical bonds or any other suitable joining means known in the art and any combination thereof.

According to the present invention the absorbent article may find utility in sanitary napkins, panty liners, adult incontinence products and baby diapers. Hence in addition to the components described herein, the absorbent article may comprise elastic, fastening devices and the like despending on the intended use of the article. In particular the present invention finds utility in sanitary napkins and panty liners.

EXAMPLES

Absorbent article according to the present invention were prepared as indicated below.

The backsheets were constructed from the following raw material:
a) non-woven fabric 28 g/m² having a spunbonded layer of 14 g/m² and a melt blown layer of 14 g/m² obtainable from Corovin GmbH, Peine, Germany under designation MD 2005.
b) polyethylene formed film according to U.S. Pat. No. 3,929,135 obtainable from Tredgar Film Products, U.S.A. The film has circular shaped apertures with an open area of 19%, an embossed thickness of 0.48 mm (funnel height) and an aperture diameter on the garment facing surface of 0.465 mm. The backsheet was prepared by joining the above described film layer (b) whereby the protruding apertures were orientated towards the wearer facing surface of the absorbent article with the non woven fabric (a) wherein the spun blown becomes the garment facing surface of the absorbent article.

Each test sample was prepared under identical conditions in all regards except for the specific treatment applied to material either forming part of or in intimate fluid contact to the backsheet construction. For the test samples sanitary pads produced under the tradename "Always Ultra Normal" available from Procter & Gamble GmbH Schwalbach/Germany were manufactured according to normal manufacturing procedures except for a very low level of attachment of the backsheet to the total structure. This allowed the existing backsheet composed of an impervious (to both liquids and gasses) plastic film to be removed and substituted for an alternative breathable backsheet. The structure of the sanitary napkin was identical for all examples except for an additional surface treatment (lowering of the surface energy of one liquid/solid surface via silicone coating).

Example 1
(Reference)

The breathable backsheet as described herein above is composed of a uni-directional (one way) conical aperatured film (CPT) made of Low Density PE produced by Tredegar USA under the manufacturing code X-1522 and positioned in contact with the absorbent core composed of tissue and absorbent gelling material. The contacting wearer facing surface is composed of a nonwoven laminate manufactured by Corovin GmbH in Germany under the trade name MD 2005. The nonwoven laminate is composed of 14 g/m² spunbond and 14 g/m² meltblown. No additional surface treatments have been applied.

Example 2

Is an identical structure to that of example 1 except the garment facing surface (30) of the absorbent core tissue (lying in contact with the wearer facing surface (31) of the aperatured uni-directional film) supplied my Walkisoft Denmark (material code: Metmar Kotka) has been treated with a basis weight of about 6 g/m² thermally cured silicone. The silicone was manufactured by DOW Corning USA and sold under the trade name SYL-OFF 7048 Crosslinker/SYL-OFF 7677, release coater (mix ratio 10%:90%).

Example 3

Is an identical structure to that of example 1 except the wearer facing surface (31) (lying in contact with the absorbent core tissue 200) of the aperatured uni-directional film (CPT) made of Low Density PE produced by Tredegar USA under the manufacturing code X-1522 has been additionally treated with a basis weight of about 3 g/m² thermally cured silicone. The silicone was manufactured by DOW Corning USA and sold under the trade name SYL-OFF 7048 Crosslinker/SYL-OFF 7677, release coater (mix ratio 10%:90%).

Example 4

Is an identical structure to that of example 1 except the aperatured uni-directional film is made of a blend of Low Density PE (84%) and silicone (16%) and was supplied by Tredegar Film Products B. V. Holland under under request of P & G Pescara Technical Centre S.p.A. The material was produced under comparable conditions to the material manufactured under code X-1522.

Example 5

Is an identical structure to that of example 3 except that the apertured uni-directional film (CPT) is made of high density polyethylene (supplied by Tredegar Film Products, U.S.A., development code 15112). As in example 3 the wearer facingr surface 31 (lying in contact with the absorbent core tissue) of the apertured uni-directional film (CPT-HDPE) has been additionally treated with a basis weigth of about 3 g/m² thermally cured silicone. The silicone was manufactured by Dow Corning USA (SYL-OFF 7048 Crosslinkers/SYL-OFF 7677, tradenames, at a ratio of 10%:90%)

Test Methods

Method Nr. 1a & 1b—Wet-Through Test

The wet-through test is utilised to evaluate the resistance of a breathable backsheet or backsheet construction to transmission of bodily discharges. It can be used as a direct measure of how liquid-impervious the porous backsheet is to the full range of bodily discharges by simply changing the composition of the test solution as will be detailed following the method description.

Basic Principle of the Methods

The basic principle of the test is to simulate the loading of a disposable absorbent article in-use with bodily discharges. To achieve this a product is prepared, for example a sanitary napkin, and placed flat on a transparent test stand made of perspex. The product is oriented with the wearer facing surface exposed (upper side) and the backsheet/garment facing surface in contact with the test stand (bottom side). Suspended above the sample to be analysed is a liquid delivery system that is capable of delivering any desired quantity of the desired test liquid (either as a burst or as a series of steps as is desired).

Located between the outer most surface of the test sample and the transparent test stand is a sheet of absorbent filter paper. This absorbent filter paper is in intimate contact with the backsheet of the test sample to simulate, for example a sanitary napkin attached to a panty or a diaper/incontinence device in close contact with the clothing. Directly below the transparent test stand is a mirror so positioned to allow any change in the absorbent filter paper (wetting with coloured solutions simulating bodily discharges) to be continuously observed. For example if the porous backsheet is unable to adequately resist liquid transmission then the filter paper will become wet with the coloured solution and this can be observed in the mirror. The magnitude of the transmitted solution either as a weight or more preferable the size of the stain on the absorbent filter paper (simulating the panty) in addition to the time dependence of the transmission can be readily recorded.

The test solution is introduced to the test sample via a calibrated delivery system such as via a simple burette according to the desired test approach as detailed below. Once the pad has been loaded with the test solution, a period of one (1) minute is allowed for the solution to be absorbed into the test sample so the topsheet (wearer facing surface) is free from pools of test solution.

Following the one minute wait the test sample is placed under a pressure of 70 g/cm$^2$ (grams per square centimeter) which is believed to reflect more stressful pressures that are nevertheless regularly obtained in-use. The test sample remains under the 70 g/cm$^2$ pressure for a period of up to 30 min. and measurements, for example the area of the coloured stain on the absorbent paper, is measured at 5 minute intervals. It is important to measure over an extended period of time because the mobility of some bodily discharges such as blood or the process of diffusion may be relatively time consuming.

It is also important to understand the mechanism of wet-through failure and to ensure the exact test design is able to correctly assess this. For example a breathable backsheet with relatively large apertures (>200 μm) is more likely to fail due to a process of extrusion (such as when sitting the pressure exerted may force the liquid through the relatively large apertures) which will happen relatively quickly on placing the test sample under pressure. Alternatively as the apertures are made ever smaller (<200 μm) a process of simple diffusion or capillary driven diffusion is more likely to occur. Such process are slow compared to extrusion processes.

Method 1a: High Gush Simulation

In this first test design the imperviousness of the porous backsheet under a high loading (sudden stressful gush of test solution) simulation is measured. This in-use situation is the most difficult to control (it often occurs on standing up after a prolonged period of lying or sitting) because typically the absorbent core (or structure) requires a finite period of time to function and to adequately absorb and bind bodily discharges. For example, an absorbent core composed of cellulose fibres (airfelt, tissue) and absorbent gelling material requires several minutes before fluids can be adequately absorbed and tightly bound. Unbound discharges, occupying void or inter fibre spaces are very mobile and can quickly move to the porous backsheet to be extruded under pressure or transported through the backsheet via capillary forces.

The high gush simulation test is performed as detailed in the above general description under the following conditions for a typical sanitary napkin:

Test Solution: Synthetic Urine+1% Surfactant or Artificial menstrual fluid+1% Surfactant Gush Volume (ml): For Sanitary Napkin 10 ml Gush Rate (ml/min.): 10 (i.e. 10 ml in 60 seconds)

Pressure applied: 70 g/cm$^2$ (after 1 min. wait)

Results reported as area of stain/wet-through in units of square cm (cm$^2$) at time elapses of 5, 10, 20 and 30 mins.

Method 1b: Repetitive Loading Simulation

In this first test design the imperviousness of the breathable backsheet under more typical loading conditions, where bodily discharges occur periodically and as repetitive steps rather than a single gush event, is measured. The repetitive loading simulation test as performed for a typical sanitary napkin is detailed according to the above general description with the following specific conditions: Specifically the test sample is subjected to a 5 ml load of the test solution (see below) placed in the centre of the test sample. A period of 1 minute allows test liquid to be absorbed and the sample is placed under pressure for 5 minutes. After this period the size (area) of wet-through is measured and recorded. The pressure is immediately removed and the sample is again subjected to a second 5 ml load of test solution. Again, after the 1 min. wait for the liquid to be absorbed the sample (now containing 10 ml of test solution) is placed under pressure for 5 minutes. After this period the size (area) of wet-through is measured and recorded. The pressure is immediately removed and the sample is again subjected to a third 5 ml load of test solution. Again after the 1 min. wait for the liquid to be absorbed the sample (now containing 15 ml of test solution) is placed under pressure for 5 minutes and the stain size (wet-through) is again measured. The cycle is continued until the pad has been loaded to 20 ml.

Test Solution: Synthetic Urine+1%Surfactant or artificial menstrual fluid+1% surfactant Gush Volume (ml): For Sanitary napkin repetitive stepwise 5 ml loadings.

Maximum Load: 20 ml

Loading Rate: 2.5 (i.e. 5 ml in 2 minutes) (ml/min.)

Pressure applied: 70 g/cm$^2$ (after 1 min. wait)

Results are reported as area of stain/wet-through in units of square cm (cm$^2$) at loadings of 5, 10, 15 and 20 ml.

Test Solution Type and Volumes Utilised in the Test Methods.

In order to reliabily assess the potential breathable backsheet designs the test solution conditions should be matched to the product end use. Sanitary napkins are designed to contain menstrual discharges. These discharges can be quite varied for different women and may contain various levels of fatty acids and detergent type contaminants from daily hygienic practices (washing, laundering etc.). These components are extremely mobile and may have very low surface tensions. It has been determined that actual menstrual discharge behaviour can be simulated using artificial menstrual fluid derived from sheep's blood and mucine with the addition of surfactant as detailed below. The volumes of test solutions up to 15 ml for a gush is sufficiently high so that 99% of all in-use gush situations will fall within this range. Likewise a sanitary napkin in-use may be repetitively loaded up to 20 ml (95% of all sanitary napkins fall in this range) but seldom higher. Typically a sanitary pad will have 10 ml load (90% of all pads) or less.

Although incontinence pads, baby diapers or pantiliners (pads worn by a woman between the period or at the start/end of the period) have different requirements to those of sanitary napkins, a test solution closer to urine discharges can be used even on sanitary napkins. Nevertheless, bodily contaminants (fatty acids, surfactants and detergent residues) are still found and it has been determined that the addition of surfactant to a synthetic urine solution correlates well to conditions found in use. Since it is a common practice to use feminine hygiene products (sanitary napkins, pantiliners) as light incontinence devices, it is also appropriate to assess potential breathable backsheet materials or constructions with a synthetic urine solution containing surfactant. The volumes again are chosen to reflect typical conditions that this application is likely to expose the products to. For diapers or more stressful incontinence applications the methods can be readily modified to simulate higher test solution loading volumes and rates of delivery.

Preparation of Test Solution Synthetic Urine+1% Surfactant (UreaB/1%)

The test solution Synthetic Urine is first prepared in a 10 kg master batch and smaller quantities are removed as required and surfactant is added. Each 10 Kg UreaB batch is composed of the following components:

| Component: | Formula | Quantity/10 Kg batch |
|---|---|---|
| Urea | | 200 g |
| Sodium Chloride | NaCl | 90 g |
| Magnesium Sulphate | $MgSO_4.7H_2O$ | 11 g |
| Calcium Chloride | $CaCl_2$ | 6 g |
| Distilled Water | $H_2O$ | 9693 g |

All reagents are "Reagent Grade" and available from standard Chemical suppliers. Additionally surfactant is supplied by Pegesis, U.S.A, Peosperse 200 ML. For individual measurements typically a 100 ml. test solution UreaB/1% Surfactant is prepared by mixing 90 ml. UreaB solution with 10 ml. Surfactant. The UreaB/1% solution must be constantly mixed to ensure the components do not separate prior to usage.

Preparation of Test Solution: Artificial Menstrual Fluid+1% Surfactant

Artificial Menstrual Fluid (AMF) is based on modified sheep's blood that has been modified to ensure it closely resembles human menstrual fluid in viscosity, electrical conductivity, surface tension and appearance. In addition we introduce a surfactant (1%) to this test fluid (supplied by by Pegesis/USA) to better reflect stress situations in which typical hygiene practice (and in some limited situations, dietary influences) may introduce additional surfactants or unexpected levels of, for example, fatty acids, that might lower the blood surface tension. Low surface tension menses is the biggest contributor to through backsheet wet-through failure on a breathable absorbent article such as a sanitary article.

Reagents
1) Difibrinated sheep's blood is available from Unipath S.p.A {Garbagnate Milanese/Italy}.
2) Lactic Acid from J. T. Baker Holland Reagent Grade (85–95% w/w)
3) Potassium Hydroxide (KOH) from Sigma Chemical Co. USA, Reagent grade
4) Phosphate Buffer Saline Tablets from Sigma Chemical Co. USA, Reagent grade
5) Sodium Chloride from Sigma Chemical Co. USA, Reagent grade
6) Gastric Mucine from Sigma Chemical Co. USA, Type III (CAS 84082-64-4)
7) Distilled Water.

Step 1
Prepare a 9±1% Lactic Acid Solution by dissolution of lactic acid powder and distilled water.

Step 2
Prepare a 10% Potassium Hydroxide (KOH) solution by dissolving KOH powder is into distilled water.

Step 3
Prepare a Phosphate buffer solution buffered to pH=7.2. by dissolving tablets as directed into 1 L distilled water.

Step 4
Prepare and slowly heat to 45±5° C. a solution of the following composition:
- 460±5 ml of phosphate buffer solution
- 7.5±0.5 ml of KOH solution Step 5
Prepare a Mucous Solution by slowly dissolution (with constant stirring) of approximately 30 grams of gastric mucine in the pre-heated (45±5° C.) solution prepared in step 4. Once dissolved the solution temperature should be increased to between 50–80° C. and the mixture covered for approximately 15 mins. Turn the heat down to maintain a relatively constant temperature between 40 and 50° C. and continue to stir for a period of 2.5 hrs.

Step 6
Remove the solution from the hot plate and allow the solution (from step 5) to now cool to less than 40° C. Add 2.0 ml of the 10% lactic acid solution and mix thoroughly for 2 mins.

Step 7
Place the solution in an Autoclave and heat to a temperature of 121° C. for 15 mins.

Step 8
Allow the solution to cool to room temperature and dilute 1 to 1 with the di-fibrinated sheep's blood.

Following AMF preparation its viscosity, pH and conductivity are measured to ensure the blood characteristics lie in a range close to that of normal menstrual blood {(see reference H. J. Bussing "zur Biochemie de Menstrualblutes" Zbl Gynaec, 179,456 (1957)}. The viscosity should lie in the range of 7 to 8 (units cStK). The pH should lie in the range of 6.9 to 7.5 and the conductivity in the range 10.5 to 13 (units mmho). If the viscosity is not within the range specified above it should not be used and a new batch of AMF needs to be prepared. This may require adjustment to the quantity of gastric mucine used. Since this is a natural product its composition may alter from one lot to another.

For individual measurements typically 100 ml AMF test solution with surfactant is prepared by mixing 90 ml AMF solution (maintained at 25° C.) with 10 ml Surfactant. The AMF/1% surfactant solution must be constantly mixed to ensure the components do not separate prior to usage. The solution should be used only within 4 hours of preparation.

Method Nr. 2: Fluid Contact Angle Determination

The contact angle test is a standard test to evaluate the nature of the interaction between a solid surface and a liquid droplet. The contact angle, a droplet forms on a surface is a reflection of several interactions. The nature of the liquid, its surface tension, the nature of the solid and surface abberations in addition to the nature of the liquid-solid interaction. Generally, a droplet on a rough surface typically exhibits a higher contact angle than a droplet on a smooth surface of the same chemical composition. If a droplet of water exhibits a contact angle greater than 90 degrees the surface is considered "hydrophobic" to the liquid. If the contact angle is less than 90 degrees then the surface is deemed "hydrophillic".

Basic Principal of the Methods:

The contact angle a liquid makes on a surface can be measured by a variety of techniques from both optical analysis of a droplet on a surface to more reliable techniques. The technique utilised to measure contact angle is the "Wilhelmy Plate Technique". The principal of this technique is to suspend a sample of the solid over a water vessel and slowly lower the sample to a defined depth into the liquid water and then remove it. The retarding force exerted by the water on the material sample on contact (zero immersion depth) is measured by a microbalance and the cosine of the contact angle is then determined from the equation:
Where F=Sample force at zero immersion depth as determined by the balance (mg)
P=Perimeter of sample at the interface (cm)
ST=Surface Tension (dynes cm)
Cos Ø=Cosine of contact angle
g=Acceleration due to gravity (at measuring location)

The equipment used to measure the contact angle is a Automated "Dynamic Contact Angle Analyser (model DCA-322)" manufactured by Cahn Instruments, Inc. Cerritos Calif. 90701-2275 USA. For each material assessed (see Table) a sample (24 mm×30 mm) is prepared and attached to a glass slide as specified in the equipment manual. Great care is made to ensure the material sample is not touched that might otherwise contaminate the material surface. Each material is measured 5 times to ensure accuracy of measurements and to minimise impact of manufacturing variability or surface irregularities.

TABLE 1

Surface contact angles of surfaces (following surface tension reduction treatment) of materials commonly available were measured.

| Example: | Surface | Contact Angle Untreated | Contact Angle Treated |
|---|---|---|---|
| A | Core Tissue Supplier: Walkisoft Denmark, Metmar Kotkar | ~zero | 131 |
| B | LDPE Film Code X-1522 Supplier: Tredegar USA | 102 | 121 |
| C | LDPE Film Code X-1522- both sides treated Supplier: Tredegar USA | 102 | 144 |
| D | LDPE Film code X1522 but unperforated: Tredegar Film Products B.V. Holland both surfaces treated | 80 | 103 |
| E | LDPE + Silicone (8%) Film (unperforated): Tredegar Film Products B.V. Holland both surfaces treated | 92 | na |
| F | LDPE + Silicone (16%) Film:- both surfaces treated Tredegar Film Products B.V. Holland | 102 | na |
| G | Film Teflon (ribbon not apertured) 3M Corp. USA | 130 | na |

The contact angle of a liquid on a surface and the ability of a porous material to transmit liquids either through capillary or extrusion processes is dependent on surface aberations or surface structure, the nature of the liquid and how it interacts with the surface as well as the mechanism of transport. The test solution utilised in this test is distilled water with a high hydrophilicity and high surface tension. This leads to contact angles that are higher than those typically found or expected to be found with menstrual fluids or urine type discharges. As such the absolute contact results detailed in the table need to be viewed with caution. A contact angle greater than 90 degrees with water does not imply that the material pores will exert a negative capillary force on menstrual type discharges. However, an increase in the contact angle will work towards lowering the extent/ efficiency of liquid transport (either capillary or extrusion based) through the material in question. na=not applicable, material already exhibits high contact angle.

TABLE 2

Wet-Through Testing Results

| Example | Test Solution | Test Design | Wet-Through (sqcm) Untreated | Wet-Through (sqcm) Treated* |
|---|---|---|---|---|
| 1 | UreaB/1% | 1a | 41 | — |
|   | AMF/1% | 1a | 70 | — |
|   | AMF/1% | 1b | 90 | — |
| 2 | UreaB/1% | 1a | 41 | zero |
|   | AMF/1% | 1a | 70 | zero |
|   | AMF/1% | 1b | 90 | 20 |
| 3 | UreaB/1% | 1a | 41 | 1.3 |
|   | AMF/1% | 1a | 70 | 16 |
|   | AMF/1% | 1b | 90 | 31 |
| 4 | UreaB/1% | 1a | na | 3 |
|   | AMF/1% | 1a | na | 11 |
|   | AMF/1% | 1b | na | 35 |
| 5 | UreaB/1% | 1a | 18 | zero |
|   | AMF/1% | 1a | 30 | zero |
|   | AMF/1% | 1b | 40 | 7 |

Method Nr. 3:—Uni-Directional Flow Test

The uni-directional flow test is utilised to quantify the directional flow properties of each surface of an aperatured film to bodily discharges. It can be used as a direct measure of how porous each surface is to the full range of bodily discharges by simply changing the composition of the test soultion as will be detailed following the method description.

Basic Principal of the Methods:

The basic principal of the test is to evaluate the performance of uni-directional/one way aperatured films to liquids which simulating bodily discharges. A "good aperatured film" is a film that shows a distinct preference to fluid transmission from one surface to the other but not in the reverse direction should the film be reversed and the test repeated. Naturally a "good aperatured film" will also, in addition to a distinct directionality to fluid transmission, show minimal fluid transmission in direction that would be utilised in the breathable backsheet construction.

To assess the directional liquid transmission rates of an aperatured film a simple test is performed in which a liquid saturated absorbent structure is placed on top of the aperatured film which lies on top of a stack of absorbent blotting paper. A pressure is exerted onto the total assembly (saturated absorbent material, film and blotting paper) and the magnitude of test liquid transmitted through the aperatured film onto and absorbed by the blotting paper is measured. In a second experiment the film direction is reversed and the experiment repeated. The magnitude of liquid transmission through surface 1 and surface 2 are recorded and assessed.

Specifically, a stack of 10 sheets with dimensions 12 cm×12 cm of commercially available filter/blotting paper {produced by Cartiera Favini S.p.A. Italy; Type Abssorbente Bianca "N30" (local vendor Ditta Bragiola SpA. Perugia, Italy)} are weighed and placed flat the test stand immediately below a suspended weigh. On top of the blotting paper stack a sample (each surfaces is labelled arbitrarily surface 1 & 2) of the aperatured film with dimensions 8.5 cm×8.5 cm to be assessed is placed. On top of the aperatured film a layer of fully saturated absorbent material is placed. The absorbent material is composed of two sheets of commercially available airlayed absorbent tissue with a basis weight of 63 gsm (each sheet) available from Walkisoft, Denmark under the supplier code Metmar Kotka is utilised to simulate a liquid saturated absorbent core. Each sheet of said tissue has dimensions of 5 cm×5 cm and are placed to lie symmetrically on top of each other. The tissue structure is then immersed completely for a period of 1 minute in synthetic urine (see method 1 detailing solutions) to ensure it is fully saturated.

The tissue is removed from the liquid and held in a vertical position for 60 seconds to allow excess fluid to drain before being placed immediately on top of the aperatured film. The saturated tissue is placed centrally on the aperatured film that is also positioned centrally on the blotting paper stack.

In the final stage of the test a perspex block (dimensions 8.5 cm×8.5 cm) is placed centrally on top of thew saturated tissue structure and the weight is automatically lowered onto the sample and exerts a pressure of 130 g/cm$^2$ for a period of 60 seconds. The lowering of the weight and time is controlled via a simple electronic device to ensure reproduceability from one test to the next.

The pressure exerted onto the total assembly (saturated absorbent material, film and blotting paper) causes the liquid in the saturated tissue to be extruded onto the film and should the directionality of liquid transmission through the aperatured film be favourable liquid can move through the film and be absorbed by the blotting paper. When the weight is removed the layers are separated and the blotting paper is inspected for liquid wetting and weighed. The weight difference (before/after) is recorded and compared to a second experiment in which the direction of the aperatured film is reversed and the magnitude of test liquid transmitted through the aperatured film in the reverse direction is measured.

TABLE 3

Example aperatured films and alternative materials currently available from a range of companies have been tested and the results are detailed in Table 3.

| Material | Test Solution | Surface 1 Wet-Through | Surface 2 wet-through | Surface 2 Treated wet-thru |
|---|---|---|---|---|
| Example 1: | | | | |
| CPT (LDPE) | | | | 3 g/m$^2$ |
| Supplier Code: X-1522 | | | | Silicone |
| Tredegar Corporation | UreaB/0% | 2.5 | 1.8 | 1.1 |
| USA | AMF/O% | 1.4 | 0.8 | 0.6 |
| Example 2: | | | | |
| CPT (HDPE) | | | | 3 g/m$^2$ |
| Supplier Code: 15112 | | | | Silicone |
| Tredegar Corporation | UreaB/0% | 2.3 | 0.8 | 0.5 |
| USA | AMF/O% | 1.3 | 0.5 | 0.3 |
| Example 3: | | | | |
| Airlayed Tissue (2 layers each layer 63 g/m$^2$ basis weight) Supplier Code: | | | | 5 g/m$^2$ Silicone lower layer only |
| Metmar Kotka, | UreaB/0% | 2.7 | 2.7 | 1.1 |
| Walkisoft Denmark | AMF/O% | 1.7 | 1.7 | 0.8 |

Test Solutions
Preparation of Test Solution Urea B/0%

The test solution Synthetic Urine Urea B/0% is prepared in the same manor as the test solution Urea B/0% except that no surfactant is added to the test solution.

Method Nr. 4:—Determination of Open Area

A disposable article designed to contain bodily wastes and featuring a breathable backsheet is designed to allow air and water vapour communication with the external environment. The extent or efficiency of this process (in terms of consumer benefit) can be linked to the open area of the disposable articles breathable backing and particularly the open area in regions that lie close to the body or where parts of the body are susceptable to occlusion. In this test only the open area of a permeable backsheet is assessed in terms of both localised levels as well as an averaged level reflecting the total product.

Basic Principal of the Methods:

The open area can be determined for both material(s) that are assembled or combined to form a breathable backsheet construction or for an absorbent article containing a breathable backsheet or construction.

Materials: the open area calculation for materials is relatively straight forward. The material sample is best viewed microscopically and a microscopically expanded image or a still photo should be recorded. The image can then be placed on a sheet of mm grid paper to facilitate simple calculation of the number of holes per sqcm and the area of each hole. Alternatively the image can be scanned digitally to determine number of holes and area of holes per sq cm. The open area is defined simply as the sum of the areas of each hole divided by the total area under analysis:

Absorbent articles: the open area of an absorbent article containing a breathable backsheet is determined primarily from an assesment of the "principal open area" in the regions that are expected to contribute to efficient communication with the environment. Regions of breathability that are considered of low importance are only assessed as part of the total product "averaged open area" value. For example in the absorbent article if breathability is provided in regions not in intimate contact with, or in regions of the absorbent article that are unlikely to contribute to skin occlusion then they should not be assessed as part of the "principal open area" calculation.

Step 1:

The product is microscopically examined and should regions of differing levels of porosity exist these are quantified and graded. Should regions of differing permeability exist one would typically expect to find usually only regions of some permeability or no permeability. Nevertheless, should this not be the case each region can be marked for later assesment.

Step 2:

For each region a microscopically expended image or still photo should be taken. The image is placed on a sheet of mm grid paper to facilitate simple calculation of are of each hole and to determine the number of holes per sq cm. Alternatively the image can be scanned digitally to determine number of holes and area of holes per sq cm.The open are is defined simply as the sum of the area of each hole divided by the total area under analysis:

This analysis is continued for each region of varying porosity or breathability.

The total product "averaged open area" value is then calculated

Step 3:

The "principal open area" is simply the the regional open area as calculated in Step 2 that occurs in regions of the pad that are anticipated to contribute the most to the benefit of a breathable absorbent article in use. This assesment of principal or secondary region is subjective but can be made in one of two ways:

Approach 1: The article is worn by a repesentative group of users (for example a woman for a sanitary napkin or light incontinence article) and an assesment is made as to where the article is in close proximity to the body and the potential for occlusion occurs. These are assessed as primary regions and should the backing be porous in any one of these regions they would then be clasified as "principal open area" regions.

Approach 2: The article is assessed purely technically from a data bank analysis that matches specific article characteristics that will impact pad conformity to the body (measures such as flexibility, article dimensions, thickness etc) to known wearing characteristics. From this purely technical analysis primary or secondary regions can be specified.

Example aperatured films and alternative materials currently available from a range of companies have been tested and the results are detailed in the table 4.

TABLE 4

| Example | Material | No Holes N/sqcm | | Ave. Hole Area | Open Area % |
|---|---|---|---|---|---|
| 1 | CPT (LDPE) | 110 | | | |
| | Supplier Code: X-1522 | | Surface 1 | 0.43 | ~47 |
| | Tredegar, Corporation USA | | Surface 2 | 0.13 | ~14 |
| 2 | EVA-HEX | 99 | | | |
| | Supplier Code: 4017050 | | Surface 1 | 0.42 | ~42 |
| | | | Surface 2 | 0.16 | ~16 |
| | Tredegar, Corporation USA | | | | |
| 3 | CPT (HDPE) | 110 | | | |
| | Supplier Code: X-15112 | | Surface 1 | 0.45 | ~49 |
| | Tredegar, Corporation USA | | Surface 2 | 0.16 | ~18 |

The above film is a tri-dimensional film with conical shaped aperature as such there are significant differences in the hole dimensions at each surface. Surface 1 is defined as the surface that faces the wearer when used as a breathable backsheet material.

What is claimed is:

1. A disposable absorbent article comprising, a liquid pervious topsheet, an absorbent core and a backsheet, said absorbent core being intermediate said topsheet and said backsheet, said backsheet comprising an outer layer and a liquid permeable polymeric film having uni-directional fluid transfer towards the absorbent core, said absorbent core comprising a fluid storage layer,
   said absorbent core and said backsheet each comprising at least one layer, the absorbent core and the backsheet each having a wearer facing surface and a garment facing surface, said each of said wearing facing surfaces and said garment facing surfaces having a fluid contact angle and
   said absorbent article having a lower portion extending from and including the garment facing surface of said fluid storage layer and including the garment facing surface of said outer layer of the backsheet,
   wherein at least one of the wearer facing surfaces of the lower portion has a fluid contact angle greater than the fluid contact angle of an adjacent said garment facing surface in the lower portion.

2. The disposable absorbent article according to claim 1, wherein the lower portion of the disposable absorbent article comprises a low surface energy material.

3. The disposable absorbent article according to claim 2, wherein said low surface energy material is selected from curable silicones, fluoropolymers, hydrocarbons or mixtures thereof.

4. The disposable absorbent article according to claim 2, wherein the lower portion comprises at least 5% by total weight of said layer of a low surface energy material.

5. The disposable absorbent article according to claim 2, wherein the lower portion of the disposable absorbent article comprises at least 0.25 g of a low surface energy material per square meter of the garment facing surface of the backsheet.

6. The disposable absorbent article according claim 1, wherein said backsheet comprises two layers, a first layer comprising the polymeric film and a second layer comprising the outer layer having a gas permeable fibrous fabric layer, the first layer being held adjacent to said absorbent core.

7. The disposable absorbent article according to claim 1, wherein said core comprises at least two portions, a first portion comprising said storage layer and a second portion comprising a fibrous layer, said fibrous layer being adjacent said backsheet.

8. The disposable absorbent article according to claim 1, wherein the fluid contact angle between the garment facing surface of the absorbent core and the wearer facing surface of the backsheet provides a surface energy gradient of at least 10°.

9. The disposable absorbent article according to claim 8, wherein said fluid contact angle is at least 20° greater than the fluid contact angle of an adjacent surface.

10. The disposable absorbent article according to claim 1, wherein said fluid contact angle of said garment facing surface of the absorbent core is at least 90°.

11. The disposable absorbent article according to claim 1, wherein said absorbent article preferably has a continuous fluid contact angle gradient in said lower portion.

12. The disposable absorbent article according to claim 1, wherein said article is a sanitary napkin or a panty liner.

13. A disposable absorbent article comprising, a liquid pervious topsheet, an absorbent core and a backsheet, said absorbent core being intermediate said topsheet and said backsheet, said backsheet comprising an outer layer and a liquid permeable polymeric film having uni-directional fluid transfer towards the absorbent core, said absorbent core comprising a fluid storage layer,
   said absorbent core and said backsheet each comprising at least one layer, the absorbent core and the backsheet each having a wearer facing surface and a garment facing surface, said each of said wearing facing surfaces and said garment facing surfaces having a fluid contact angle and
   said absorbent article having a lower portion extending from and including the garment facing surface of said fluid storage layer including the garment facing surface of said outer layer of the backsheet,
   wherein the garment facing surface of at least one of said layers in said lower portion has a fluid contact angle greater than the fluid contact angle of the wearer facing surface of said same layer.

14. The disposable absorbent article according to claim 13, wherein the lower portion of the disposable absorbent article comprises a low surface energy material.

15. The disposable absorbent article according to claim 13, wherein said low surface energy material is selected from curable silicones, fluoropolymers, hydrocarbons or mixtures thereof.

16. The disposable absorbent article according to claim 14, wherein the lower portion of the disposable absorbent article comprises at least 0.25 g of a low surface energy material per square meter of the garment facing surface of the backsheet.

17. The disposable absorbent article according claim 13, wherein said backsheet comprises two layers, a first layer comprising the polymeric film and a second layer comprising the outer layer having a gas permeable fibrous fabric layer, the first layer being held adjacent to said absorbent core.

18. The disposable absorbent article according to claim 13, wherein said core comprises at least two portions, a first portion comprising said storage layer and a second portion comprising a fibrous layer, said fibrous layer being adjacent said backsheet.

19. The disposable absorbent article according to claim 13, wherein the fluid contact angle between the garment facing surface of the absorbent core and the wearer facing surface of the backsheet provides a surface energy gradient of at least 10°.

20. The disposable absorbent article according to claim 19, wherein said fluid contact angle is at least 20° greater than the fluid contact angle of an adjacent surface.

21. The disposable absorbent article according to claim 13, wherein said fluid contact angle of said garment facing surface of said storage layer is at least 90°.

22. The disposable absorbent article according to claim 13, wherein said absorbent article preferably has a continuous fluid contact angle gradient in said lower portion.

23. The disposable absorbent article according to claim 13, wherein said article is a sanitary napkin or a panty liner.

* * * * *